US009581385B2

(12) United States Patent
Malik

(10) Patent No.: US 9,581,385 B2
(45) Date of Patent: Feb. 28, 2017

(54) METHODS FOR SEPARATING HYDROCARBON GASES

(71) Applicant: Zaheer I. Malik, Tulsa, OK (US)

(72) Inventor: Zaheer I. Malik, Tulsa, OK (US)

(73) Assignee: Linde Engineering North America Inc., Blue Bell, PA (US)

( * ) Notice: Subject to any disclaimer, the term of this patent is extended or adjusted under 35 U.S.C. 154(b) by 532 days.

(21) Appl. No.: 13/894,692

(22) Filed: May 15, 2013

(65) Prior Publication Data

US 2014/0338396 A1 Nov. 20, 2014

(51) Int. Cl.
*F25J 3/00* (2006.01)
*F25J 3/02* (2006.01)

(52) U.S. Cl.
CPC ........... *F25J 3/0209* (2013.01); *F25J 3/0233* (2013.01); *F25J 3/0238* (2013.01); *F25J 3/0242* (2013.01); *F25J 2200/02* (2013.01); *F25J 2200/30* (2013.01); *F25J 2200/70* (2013.01); *F25J 2200/72* (2013.01); *F25J 2200/74* (2013.01); *F25J 2200/78* (2013.01); *F25J 2205/04* (2013.01); *F25J 2240/02* (2013.01); *F25J 2270/02* (2013.01); *F25J 2270/12* (2013.01); *F25J 2270/88* (2013.01); *F25J 2280/02* (2013.01); *F25J 2290/40* (2013.01)

(58) Field of Classification Search
CPC ........ F25J 3/0209; F25J 3/0233; F25J 3/0238; F25J 3/0242; F25J 2200/02; F25J 2200/70; F25J 2200/30; F25J 2205/04; F25J 2240/02; F25J 2200/72; F25J 2200/74; F25J 2200/78
USPC .................................................. 62/618, 620
See application file for complete search history.

(56) References Cited

U.S. PATENT DOCUMENTS

| | | | | |
|---|---|---|---|---|
| 3,292,380 | A | 12/1966 | Bucklin | |
| 4,061,481 | A | 12/1977 | Campbell et al. | |
| 4,140,504 | A | 2/1979 | Campbell et al. | |
| 4,157,904 | A | 6/1979 | Campbell et al. | |
| 4,171,964 | A * | 10/1979 | Campbell | F25J 3/0209 62/621 |
| 4,185,978 | A | 1/1980 | McGalliard et al. | |
| 4,251,249 | A | 2/1981 | Gulsby | |
| 4,278,457 | A | 7/1981 | Campbell et al. | |
| 4,519,824 | A | 5/1985 | Huebel et al. | |
| 4,617,039 | A | 10/1986 | Buck | |
| 4,687,499 | A | 8/1987 | Aghili | |

(Continued)

*Primary Examiner* — Keith Raymond
(74) *Attorney, Agent, or Firm* — Philip H. Von Neida

(57) ABSTRACT

The present invention relates to a process for separating a hydrocarbon gas into a fraction containing a predominant portion of the methane or ethane and lighter components and a fraction containing a predominant portion of the $C_2$ or $C_3$ and heavier components in which process the feed gas is treated in one or more heat exchange, and expansion steps; partly condensed feed gas is directed into a separator wherein a first residue vapor is separated from a $C_2$ or $C_3$-containing liquid; and $C_2$ or $C_3$-containing liquids, at substantially the pressure of separation, are directed into a distillation column wherein said liquid is separated into a second residue is separated to recover a $C_2$ or $C_3$-containing product. The foregoing process is improved by cooling said second residue to partially condense it.

24 Claims, 2 Drawing Sheets

(56) References Cited

U.S. PATENT DOCUMENTS

| | | | | |
|---|---|---|---|---|
| 4,689,063 | A | 8/1987 | Paradowski et al. | |
| 4,690,702 | A | 9/1987 | Paradowski et al. | |
| 4,854,955 | A | 8/1989 | Campbell et al. | |
| 4,869,740 | A | 9/1989 | Campbell et al. | |
| 4,889,545 | A | 12/1989 | Campbell et al. | |
| 4,895,584 | A | 1/1990 | Buck et al. | |
| RE33,408 | E | 10/1990 | Khan et al. | |
| 5,275,005 | A | 1/1994 | Campbell et al. | |
| 5,555,748 | A | 9/1996 | Campbell et al. | |
| 5,566,554 | A | 10/1996 | Vijayaraghavan et al. | |
| 5,568,737 | A | 10/1996 | Campbell et al. | |
| 5,771,712 | A | 6/1998 | Campbell et al. | |
| 5,799,507 | A | 9/1998 | Wilkinson et al. | |
| 5,881,569 | A | 3/1999 | Campbell et al. | |
| 5,890,378 | A | 4/1999 | Rambo et al. | |
| 5,983,664 | A | 11/1999 | Campbell et al. | |
| 6,182,469 | B1 | 2/2001 | Campbell et al. | |
| 6,278,035 | B1 | 8/2001 | Key et al. | |
| 6,311,516 | B1 | 11/2001 | Key et al. | |
| 6,578,379 | B2 | 6/2003 | Paradowski | |
| 6,712,880 | B2 * | 3/2004 | Foglietta ................ | F25J 3/0209 62/618 |
| 6,915,662 | B2 | 7/2005 | Wilkinson et al. | |
| 7,191,617 | B2 | 3/2007 | Cuellar et al. | |
| 7,219,513 | B1 | 5/2007 | Mostafa | |
| 9,103,585 | B2 * | 8/2015 | Mak ....................... | F25J 3/0209 |

* cited by examiner

METHODS FOR SEPARATING HYDROCARBON GASES

BACKGROUND OF THE INVENTION

The present invention relates to a method and apparatus for the improved recovery of $C_2$ or $C_3$ and heavier components from hydrocarbon gases.

In conventional processes for extracting ethane or propane and heavier components from hydrocarbon gases, the $C_2$ and/or $C_3$ bearing gases are treated by a combination of expansion (or compression followed by expansion) heat exchange and refrigeration to obtain a partially condensed stream which is collected in a feed separator having a pressure typically in the order of 50 to 1200 psia and a temperature in the order of −50° to −200° F. These conditions of course can vary substantially, depending on the pressure and temperature conditions necessary to achieve partial condensation for a particular gas, and the pressure and temperature at which the feed is available to the process. The liquid resulting from partial condensation is supplied to a fractionation column called a heavy ends fractionation column (HEFC) as a mid-column feed while the vapor from the feed separator is further cooled via heat exchange, expansion or other means and then enters a light ends fractionation column (LEFC) as a feed. The overhead stream from the LEFC is used to generate reflux by partially condensing the overhead vapors from the HEFC through appropriate heat exchange means. In a typical system the HEFC column will operate at a pressure less than or substantially equal to that of the HEFC feed separator (possibly allowing for a small pressure drop as the partially condensed liquid passes from the separator to the HEFC) and the HEFC overhead vapors leave at a temperature in the order of 0° to −170° F. The heat exchange of these overhead vapors against the residue vapors from the LEFC provides partial condensate which is used as a reflux to the LEFC.

Pre-cooling of the gas before it is expanded to the LEFC pressure will commonly result in formation of a high-pressure condensate. To avoid damage to the expander, the high pressure condensate, if it forms, is usually separated, separately expanded through a Joule-Thomson valve and used as a further feed to the mid-portion of the HEFC column. Refrigeration in such a process is sometimes entirely generated by work expansion of the vapors remaining after partial condensation of the high pressure gas to the column operating pressure. Other processes may include external refrigeration of the high pressure gases to provide some of the required cooling.

When processing natural gas, feed is typically available at line pressure, of 600-1000 psia. In such case expansion to a pressure in the order of 150-300 psia is common. In an alternate process, facilities may be designed to extract ethane or ethylene or propane or propylene from refinery gases. Refinery gases commonly are available a pressure of 150 psia-250 psia. In this case, at the convenience of the process designer, the LEFC may be designed to operate at a pressure below the pressure of the refinery gas which is available, i.e., perhaps 50-100 psia, so that work expansion can be used to supply refrigeration to the process. This will result in lower LEFC temperatures and will increase potential heat leakage and other engineering problems associated with cryogenic temperatures. It is also possible in this case to compress the refinery gas to a higher pressure so that it may be thereafter expanded in a work-expansion machine to afford refrigeration to the overall process.

A typical flow plan of a process for separating $C_3$ and heavier hydrocarbons from a gas stream is illustrated in U.S. Pat. No. 4,251,249 to Jerry G. Gulsby.

SUMMARY OF THE INVENTION

In one embodiment of the invention, there is described a process for separating a hydrocarbon gas containing at least methane, ethane and $C_3$ components into a fraction containing a predominant portion of the ethane and lighter components and a fraction containing a predominant portion of the $C_3$ and heavier components or a predominant portion of the methane and lighter components and a fraction containing a predominant portion of the $C_2$ and heavier components, in which process (a) the feed gas is treated in one or more heat exchangers, and expansion steps to provide at least one partly condensed hydrocarbon gas, providing thereby at least one first residue vapor and at least one $C_2$ or $C_3$-containing liquid which liquid also contains lighter hydrocarbons; and (b) at least a portion of the $C_2$ or $C_3$-containing liquids is directed into a distillation column wherein said liquid is separated into a second residue containing lighter hydrocarbons and a $C_2$ or $C_3$-containing product; comprising:

(1) cooling said second residue to partially condense it;

(2) intimately contacting at least part of one of said first residue vapors with at least part of the liquid portion of the partially condensed second residue in at least one contacting stage and thereafter separating the vapors and liquids from said contacting stage;

(3) supplying the liquids thereby recovered to the distillation column as a liquid feed thereto; and (4) directing the vapors thereby recovered into heat exchange relation with said second residue from the distillation column, thereby to supply the cooling of step (1), and thereafter discharging said residue gases; the improvement further comprising:

(5) recovering a recycle gas stream from an expander-compressor or residue gas compressor;

(6) cooling and partially condensing the recycle stream in said one or more heat exchangers;

(7) expanding the recycle stream thereby further condensing a portion of and cooling the recycle stream;

(8) feeding the expanded recycle stream to a subcooler, whereby the expanded recycle stream is heat exchanged in the subcooler with gases from top of the heavy-ends fractionation column thereby providing colder temperatures to the vapors from the heavy ends fractionation column, The contacting step (2) is carried out in a feed separator/absorber which includes fractionation means for vapor/liquid counter-current contact and (i) wherein said partly condensed second residue is introduced into said separator/absorber above or at an intermediate point in said fractionation means, whereby the liquid portion of it passes downwardly through said fractionation means; and (ii) wherein said partly condensed portion of the first residue is introduced into said separator/absorber above or at an intermediate point in said fractionation means, whereby the liquid portion of it passes downwardly through said fractionation means; and wherein said portion of the cooled $C_2$ or $C_3$-containing liquid from the separator is introduced into said separator/absorber above or at an intermediate point in said fractionation means, whereby the liquid portion of it passes downwardly through said fractionation means; and (iii) said at least part of one of said first residue vapors is supplied to said separator/absorber below said fractionation means, whereby the first residue vapor rises through said fractionation means in counter-current contact with the liquid portion of the partly condensed second residue.

The fractionation means in said separator/absorber provide the equivalent of at least one theoretical distillation stage arranged to contact at least part of one of said first residue vapors with the liquid portion of the partly condensed second residue.

The fractionation means in said separator/absorber provide the equivalent of at least one theoretical distillation stage arranged to contact at least part of one of said first residue vapors with the liquid portion of the partly condensed second residue.

The recycle gas stream recovered may further pass through expander-compressor discharge cooler or other compression discharge cooler prior to it being partially condensed in the one or more heat exchangers. The one or more heat exchangers where the recycle stream is partially condensed may have other liquid and gas flows present therein which can further be used, in addition to the gases from the top of the light-ends fractionation column to partially condense the recycle stream. For example, the liquid product from the light-ends fractionation column, the reboiler fluid, the side heater fluid and/or the residue gas streams may all pass through the one or more heat exchangers.

The one or more heat exchangers may be shell and tube, plate-fin exchangers or other means of heat exchange. The expansion of the recycle stream may be through a flow control valve or additional turboexpander.

The cold expanded recycle stream that is fed to the subcooler will combine with the overhead stream from the light-ends fractionation column resulting in a cooler reflux stream that is fed into the light-ends fractionation column thereby promoting increased reflux and thus, a greater recovery from the light-ends fractionation column.

Further, there is described an apparatus for separating a hydrocarbon gas containing at least ethane and $C_3$ components into a fraction containing a predominant portion of ethane and lighter components and a fraction containing a predominant portion of the $C_3$ and heavier components in which apparatus (a) one or more heat exchange means and one or more expansion means are provided which are cooperatively connected to provide at least one partly condensed hydrocarbon gas, providing thereby at least one first residue vapor and at least one $C_3$-containing liquid which liquid also contains lighter hydrocarbons and (b) a distillation column connected to receive at least one of said $C_3$-containing liquids which is adapted to separate the $C_3$-containing liquids into a second residue containing lighter hydrocarbons and a $C_3$-containing product;

the improvement comprising (1) heat exchange means connected to said distillation column to receive said second residue and to partially condense it;

(2) contacting and separating means connected to receive at least part of one of the first residue vapors and at least part of the liquid portion of the partially condensed second residue and to comingle said vapor and liquid in at least one contacting stage, which means include separation means for separating the vapor and liquid after contact in said stage;

(3) said means (2) being further connected to supply the liquids separated therein to the distillation column as a liquid feed thereto, and (4) said means (2) also being connected to direct the vapors separated therein into heat exchange relation with said second residue from the distillation column in said heat exchange means (1); the improvement further comprising (5) Product cooler means connected to said distillation column to receive said second residue from said distillation column and to feed said second residue to said heat exchange means.

The contacting and separating means includes fractionation means for countercurrent vapor/liquid contact and wherein said means is connected to receive the portion of one of first residue vapors to be treated therein below said fractionation means and to receive the portion of said liquids from the partially condensed second residue to be treated therein above said fractionation means said fractionation means thereby being adapted so that the first residue vapors rise therethrough in countercurrent contact with partially condensed second residue.

The fractionation means includes vapor/liquid contacting means which are the equivalent of at least one theoretical distillation stage.

The contacting and separating means (2) comprise means for comingling at least part of one of said first residue vapors with the liquid portion of the partially condensed second residue.

The contacting and separating means (2) comprise means for comingling at least part of one of said first residue vapors with both the liquid and vapor portion of said partially condensed second residue.

The contacting and separating means includes fractionation means for countercurrent vapor/liquid contact and wherein said means is connected to receive the portion of one of first residue vapors to be treated therein below said fractionation means and to receive the portion of said liquids from the partially condensed second residue, portion of the partially condensed first residue and portion of the cooled $C_3$-containing liquid from the separator to be treated therein above or at an intermediate point in said fractionation means said fractionation means thereby being adapted so that the first residue vapors rise there-through in countercurrent contact with partially condensed second residue and portion of the partially condensed first residue and being further adapted so that the portion of the $C_3$-containing liquid from the separator is cooled by the liquids exiting the fractionation means.

The fractionation means includes vapor/liquid contacting means which are the equivalent of at least one theoretical distillation stage.

The contacting and separating means (2) comprise means for comingling at least part of one of said first residue vapors with the liquid portion of the partially condensed second residue, liquid portion of the partially condensed portion of the first residue and portion of the cooled $C_3$-containing liquid from the separator.

The contacting and separating means (2) comprise means for comingling at least part of one of said first residue vapors with both the liquid and vapor portion of said partially condensed second residue, said partially condensed portion of the first residue and portion of the cooled $C_2$ or $C_3$-containing liquid from the separator.

DESCRIPTION OF THE INVENTION

Figure 1A:
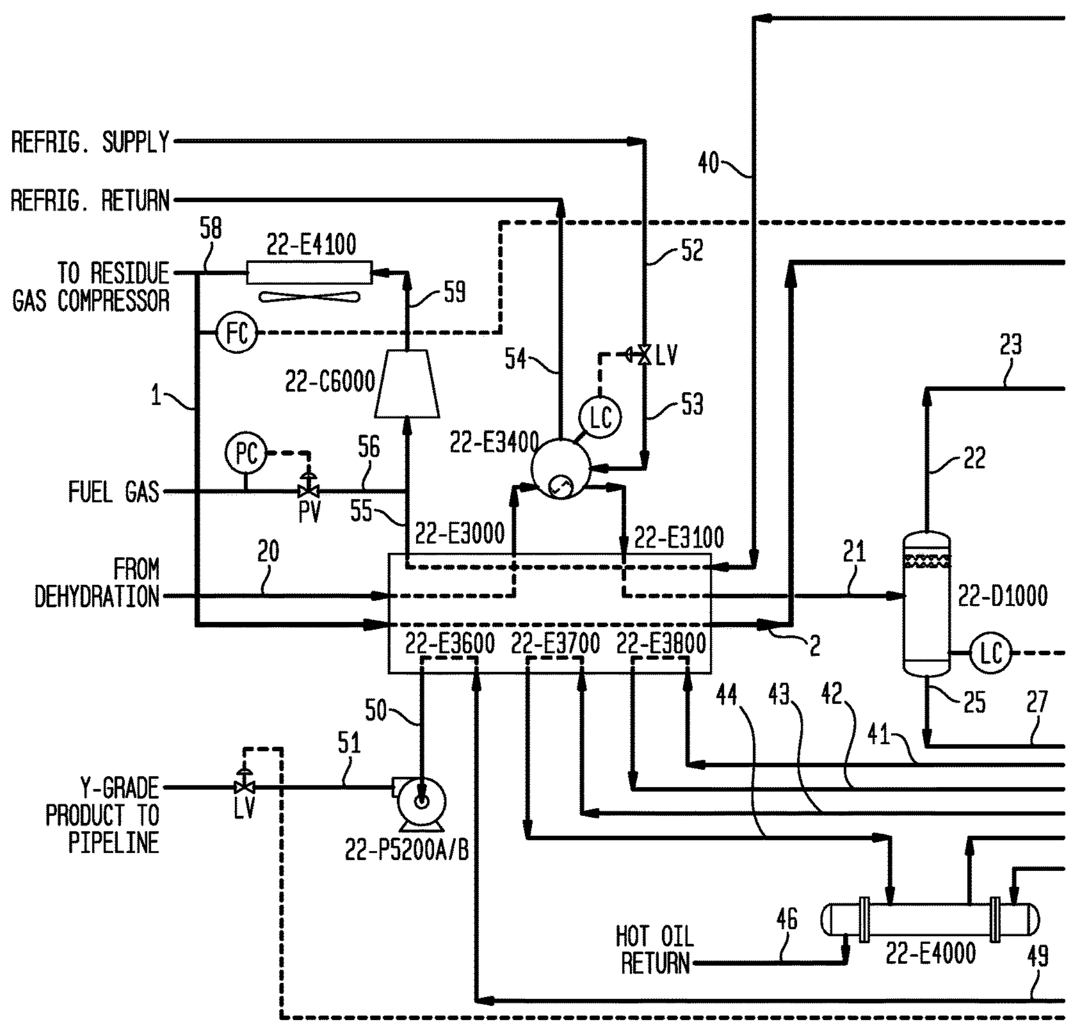
FIG. 1A is a partial schematic representation of a hydrocarbons separation process according to the invention which shows half the process due to scaling constraints.

The present invention provides an improved process for recovering $C_2$ or $C_3$ and heavier components from hydrocarbon-bearing gases. In the improved process of the present invention the overhead vapor from the HEFC column is partly condensed and then at least the liquid condensate is combined with at least the vapor from the partially condensed feed gases described above in the LEFC which, in the present invention, also acts as an absorber. The LEFC is designed to afford one or more contacting stages. Usually such stages are assumed for design purposes to be equilibrium stages, but in practice this need not be so. Vapor from the feed separator/absorber passes in heat exchange relation to the overhead from the HEFC, thereby providing partial condensation of that stream, and liquid from the LEFC is supplied to the HEFC as an upper or top liquid feed to the column.

If the LEFC contains an absorption section, such as packing, or one or more fractionation trays, these stages will be assumed to correspond to a suitable number of theoretical separation stages. Our calculations have shown benefits with as few as one theoretical stage, and greater benefits as the number of theoretical stages is increased. We believe that benefits can be realized even with the equivalent of a fractional theoretical stage. The partially condensed HEFC overhead is supplied above this section, and the liquid portion of it passes downward through the absorption section. The partially condensed feed stream is usually supplied below the absorption section, so that the vapor portion of it passes upwardly through it in countercurrent contact with the liquids from the partially condensed HEFC overhead. The rising vapor joins the vapors which separate from partially condensed HEFC overhead above the absorption section, to form a combined residue stream.

While described above with respect to a preferred embodiment in which overhead vapors are condensed and used to absorb valuable ethane, ethylene, propane, propylene, etc, from the expander outlet vapors, we point out that the present invention is not limited to this exact embodiment. Advantages can be realized, for instance, by treating only a part of the expander outlet vapor in this manner, or using only part of the overhead condensate as an absorbent in cases where other design considerations indicate that portions of the expander outlet or overhead condensate should bypass the LEFC. We also point out that the LEFC can be constructed as either a separate vessel, or as a section of the HEFC column.

In the practice of this invention there will necessarily be a slight pressure difference between the LEFC and the HEFC which must be taken into account. If the overhead vapors pass through the condenser and into the separator without any boost in pressure, the LEFC will assume an operating pressure slightly below the operating pressure of the HEFC. In this case the liquid feed withdrawn from the LEFC can be pumped to its feed position in the HEFC. An alternative is to provide a booster blower in the vapor line to raise the operating pressure in the overhead condenser and LEFC sufficiently so that the liquid feed can be supplied to the HEFC without pumping. Still another alternate is to mount the LEFC at a sufficient elevation relative to the feed position of the liquid withdrawn therefrom that the hydrostatic head of the liquid will overcome the pressure difference.

In still another alternate, all or a part of the partially condensed HEFC overhead and all or part of the partially condensed feed can be combined, such as in the pipe line joining the expander output to the LEFC and if thoroughly intermingled, the liquids and vapors will mix together and separate in accordance with a relative volatility of the various components of the total combined streams. In this embodiment the vapor-liquid mixture from the overhead condenser can be used without separation, or the liquid powder thereof may be separated. Such co-mingling is considered for purposed of this invention as a contacting stage.

In still another variation of the foregoing, the partially condensed overhead vapors can be separated, and the all or a part of the separated liquid supplied to the LEFC or mixed with the vapors fed thereto.

The present invention provides improved recovery of ethane or ethylene, propane or propylene per amount of power input required to operate the process. An improvement in operating power required for operating a HEFC process may appear either in the form of reduced power requirements for external refrigeration, reduced power requirements for compression or recompression, or both. Alternatively, if desired, increased C2 or C3 recovery can be obtained for a fixed power input.

Figure 1B:
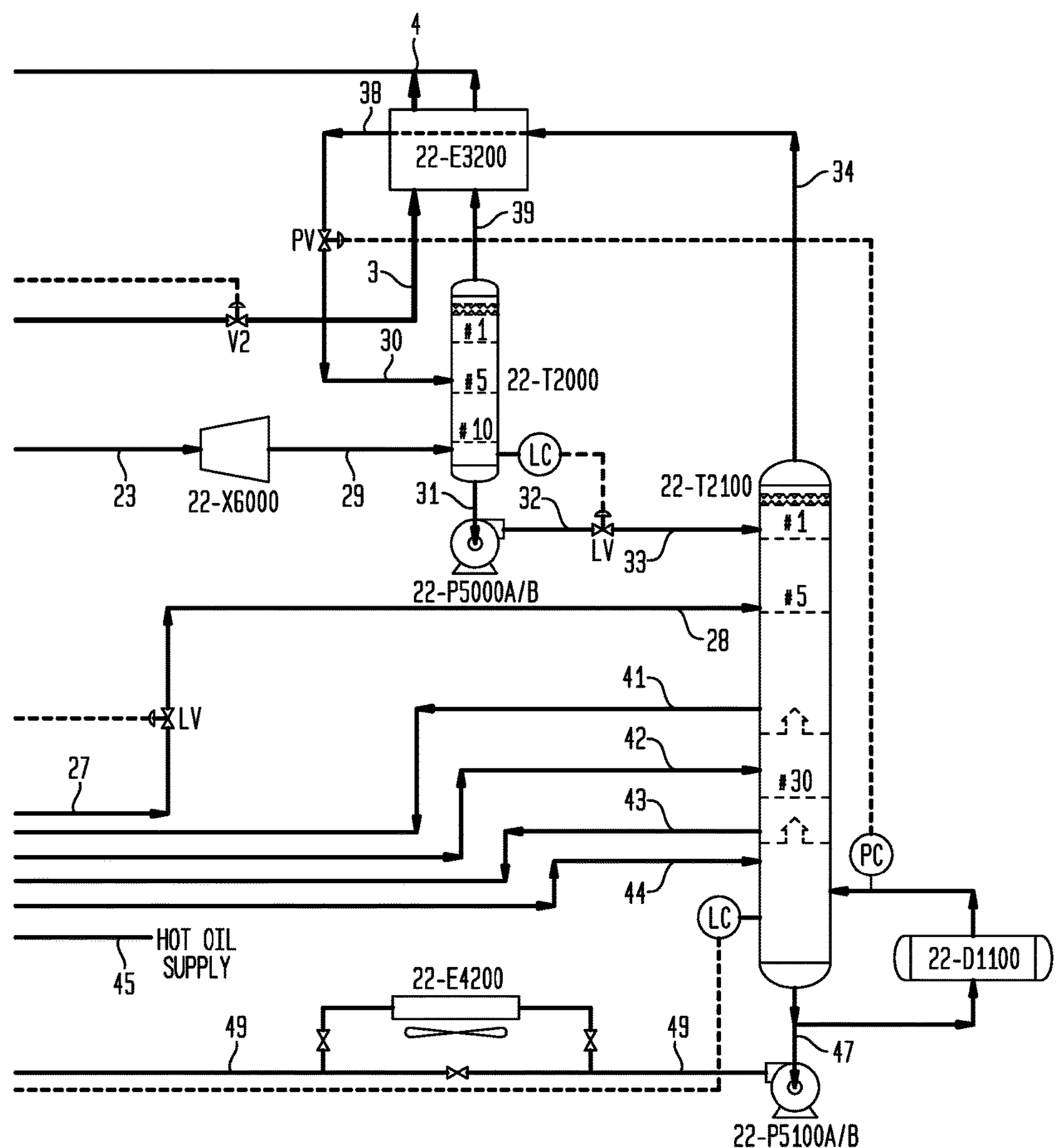
FIG. 1B is a partial schematic representation of the other half of a hydrocarbons separation process according to the invention which shows the other half of the process due to scaling constraints.

FIG. 1A and FIG. 1B represent a schematic of a hydrocarbon separation process according to the invention. A hydrocarbon bearing gas natural gas is fed through line 20 to a warm gas/gas exchanger 22-E3000 and then to a chiller 22-E3400. Refrigeration is supplied through line 52 and 53. The chiller has a line 54 which will withdraw refrigeration for recompression and liquefaction. The cooled gas stream is fed through line 21 through a cold gas/gas exchanger 22-3100 to a cold separation vessel 22-D1000.

The hydrocarbon gas stream will be separated into two streams with the vapor leaving through line 22 and the bottoms through line 25 to line 27. The bottoms will pass through a valve LV in line 27 for flow control and will rejoin line 27 to line 28 where they will enter heavy ends fractionation column 22-T2100.

The tops from the cold separation vessel 22-D1000 will leave through line 22 and reach a junction with line 23. The remainder of the tops from the cold separation vessel flow through line 23 through an expander/compressor 22-X6000. This expanded hydrocarbon gas stream will be fed through line 29 into the light ends fractionation column 22-T2000.

The vapor from the light ends fractionation column 22-T2000 will leave through line 39 and pass through line 40 where they will pass through cold gas/gas exchanger 22-E3100 and warm gas/gas exchanger before passing through line 55 to an expander/compressor 22-06000 where the compressed gas stream will enter and expander/compressor discharge cooler 22-E4100 through line 59. The discharged gas stream will exit through line 58 and for sales or further processing as required.

Line 56 contacts line 55 and some of the hydrocarbon gas will be drawn off before entering the expander/compressor 22-C6000 and recovered for use as fuel gas. A valve assembly is present in line 56 for controlling the quantity of the material to be used as fuel gas.

The bottoms from the light ends fractionation column 22-T2000 will exit through line 31. These bottoms comprise an intermediate liquid stream that required further fractionation. Line 31 is in fluid communication with a transfer pump 22-P5000A/B which directs the bottoms from the light ends fractionating column to line 33 and into the top of a heavy ends fractionation column 22-T2100.

A stream comprising a cooler, intermediate product liquid is withdrawn from the heavy ends fractionation column 22-T2100 through line 41 which is fed to a side heater 22-E3800 which will heat the stream and return it through line 42 to a point lower in the heavy ends fractionation column from which it was withdrawn. Another side steam is withdrawn from the heavy ends fractionation column 22-T2100 through line 43 which is fed to a heavy ends fractionation column reboiler 22-E3700 which will heat the side stream. This stream is fed to a trim reboiler 22-E4000 where it will be further heated before being returned through line 44 to a point lower in the heavy ends fractionation column from which it was withdrawn. Line 45 will supply heating media (not shown) to the trim reboiler 22-E4000 while line 46 will return heating media from the trim reboiler.

A line at the bottom of the heavy ends fractionating column will remove some of the hydrocarbon comprising mainly of C2s and less volatile hydrocarbons or C3s and less volatile hydrocarbon and direct it to a valve in line 51. Line 51 receives bottoms from the heavy ends fractionating column 22-T2100. Line 47 feeds the bottoms from the heavy ends fractionating column and feeds them to a heavy ends fractionating column bottoms pump 22-P5100A/B which feeds the bottoms through line 49 to a product exchanger 22-E3600 which feeds the bottoms through line 50 to the product pump 22-P5200A/B. This pump directs the bottoms through line 51 where they can be directly fed to a pipeline. A valve in line 49 will allow bypass of the product exchanger 22-E3600 and divert the flow to an air or water cooled heat exchanger when the plant is operated in the C3 and heavier recovery mode. After cooling, these bottoms can be fed back into line 49 for feeding to the product exchanger 22-E3600.

The vapor from the heavy ends fractionation column 22-T2100 will exit through line 34 and pass through a subcooler 22-E3200. Line 38 exits the subcooler 22-E3200 and connects to a valve. The vapor from the heavy ends fractionation column will be fed through line 30 into the light ends fractionation column 22-T2000 where they will be further fractionated for reentry back into the heavy ends fractionation column as a reflux stream.

A portion of the compressed residue gas from stream 58 is recycled through the overall cryogenic process not only to increase ethane and heavier hydrocarbon component recoveries, but also to reduce the energy consumption of the overall system.

The improved process utilizes the recycle stream 1 in which a portion of the residue gas is cooled and may be partially liquefied in via heat exchange, expanded reducing its temperature and thus increasing the reflux in the light-ends fractionation column, 22-T2000. This recycle stream 1 is fed downstream from the expander-compressor, 22-X10600 and expander-compressor discharge cooler, 22-E4100 or downstream of the residue gas compressor aftercooler. The recycle stream 1 is cooled and partially condensed in the inlet plate-fin heat exchanger, 22-E3000 where the recycle stream 1 can be cross-exchanged with an inlet stream 20, liquid product stream 49, the reboiler fluid stream 43, the side heater fluid stream 41 and the residue gas stream 40 together. The recycle stream leaves the heat exchanger 22-E3000 through line 2 and is expanded across a flow-control valve V2 where further liquefaction and cooling to the recycle stream will occur. This further cooled and liquefied recycle stream passes through flow-control valve V2 and enters line 3 which is fed into the subcooler 22-E3200. The subcooler 22-E3200 provides additional refrigeration by mixing with the vapor from the light-ends fractionation column 22-T2000. By reaching these cold temperatures, additional liquefaction occurs thus providing more reflux to the light ends fractionation column 22-T2000. Said reflux will result in more ethane adsorption as well as increasing ethane and heavier component recoveries.

The recycle stream having provided more cooling to the subcooler 22-E3200 and subsequently cooler reflux for the light-ends fractionation column 22-T2000 flows through subcooler 22-E3200 and enters line 4 where it will flow to line 40 where it will be fed through heat exchanger 22-E3000 where it will be further heated and then fed through line 55 to expander/compressor 22-C6000. The compressed stream will be fed through line 59 to expander/compressor discharge cooler 22-E4100 where it will be recompressed and fed into line 1 where it will recycle ultimately to subcooler 22-E3200.

While this invention has been described with respect to particular embodiments thereof, it is apparent that numerous other forms and modifications of the invention will be obvious to those skilled in the art. The appended claims in this invention generally should be construed to cover all such obvious forms and modifications which are within the true spirit and scope of the invention.

Having thus described the invention, what I claim is:

1. In a process for separating a hydrocarbon gas containing at least ethane and $C_3$ and heavier components into a fraction containing a predominant portion of the ethane and lighter components and a fraction containing a predominant portion of the $C_3$ and heavier components in which process (a) the hydrocarbon gas is treated in one or more heat exchangers, and expansion steps to provide at least one partly condensed hydrocarbon gas, providing thereby at least one first residue vapor and at least one $C_2$ or $C_3$-containing liquid which liquid also contains lighter hydrocarbons; and (b) at least one of the $C_2$ or $C_3$-containing liquids is directed into a distillation column wherein said liquid is separated into a second residue containing lighter hydrocarbons and a $C_2$ or $C_3$-containing product;

the improvement comprising (1) cooling said second residue to partially condense said second residue;

(2) intimately contacting at least part of one of said first residue vapors with at least part of a liquid portion of the partially condensed second residue in at least one contacting stage and thereafter separating vapors and liquids from said contacting stage;

(3) supplying the liquids from said contacting stage to the distillation column as a liquid feed thereto; and (4) directing the vapors from said contacting stage into heat exchange relation with said second residue from the distillation column, thereby to supply the cooling of step (1), and thereafter discharging said vapors from the contacting stage;

the improvement further comprising:

(5) recovering a recycle gas stream from an expander-compressor or residue gas compressor;

(6) cooling and partially condensing the recycle stream in said one or more heat exchangers;

(7) expanding the recycle stream thereby further condensing a portion of and cooling the recycle stream;

(8) feeding the expanded recycle stream to a subcooler, whereby the expanded recycle stream is heat exchanged in the subcooler with gases from top of a light-ends fractionation column; thereby providing colder temperatures to the second residue from the distillation column.

2. The process as claimed in claim 1 wherein said contacting step (2) is carried out in the light end fractionation column which includes fractionation means for vapor/liquid counter-current contact and (i) wherein said partly condensed second residue is introduced into said light ends fractionation column above said fractionation means, whereby the liquid portion of the partly condensed second residue passes downwardly through said fractionation means; and (ii) said at least part of one of said first residue vapors is supplied to said light ends fractionation column below said fractionation means, whereby the first residue vapor rises through said fractionation means in counter-current contact with the liquid portion of the partly condensed second residue.

3. The process as claimed in claim 2 wherein the fractionation means in said light ends fractionation column provide the equivalent of at least one theoretical distillation stage arranged to contact at least part of one of said first residue vapors with the liquid portion of the partly condensed second residue.

4. The process according to claim 1 wherein at least part of one of said first residue vapors are co-mingled with the liquid portion of the partially condensed second residue.

5. The process as claimed in claim 1 wherein at least part of one of said first residue vapors are comingled with both the liquid portion and vapor portion of said partially condensed second residue.

6. The process as claimed in claim 1 wherein the colder temperatures provided by the expanded recycle stream improve the yield of ethane and heavier components from the light-ends fractionation column.

7. The process as claimed in claim 1 wherein said recycle gas stream recovered is further fed through an expander/compressor discharge cooler or residue gas compressor discharge cooler prior to said recycle gas stream being condensed in said one or more heat exchangers.

8. The process as claimed in claim 1 wherein said one or more heat exchangers receives additional gas and liquid flows to cool and partially condense the recycle stream.

9. The process as claimed in claim 7 wherein said additional gas and liquid flows are selected from the group consisting of inlet gas stream, liquid product stream, reboiler fluid stream, side heater fluid stream, refrigerant stream(s) and residue gas stream.

10. The process as claimed in claim 1 wherein said one or more heat exchangers is a plate-fin exchanger, shell and tube heat exchanger or coil wound heat exchanger.

11. The process as claimed in claim 1 wherein said expanding of the recycle stream is through a flow control valve or turboexpander.

12. The process as claimed in claim 1 wherein a cold reflux stream is from the distillation column.

13. In a process for separating a hydrocarbon gas containing at least methane and $C_2$ and heavier components into a fraction containing a predominant portion of the methane and lighter components and a fraction containing a predominant portion of the $C_2$ and heavier components in which process (a) the hydrocarbon gas is treated in one or more heat exchangers, and expansion steps to provide at least one partly condensed hydrocarbon gas, providing thereby at least one first residue vapor and at least one $C_2$-containing liquid which liquid also contains lighter hydrocarbons; and (b) at least one of the $C_2$-containing liquids is directed into a distillation column wherein said liquid is separated into a second residue containing lighter hydrocarbons and a $C_2$-containing product;

the improvement comprising (1) cooling said second residue to partially condense said second residue;

(2) intimately contacting at least part of one of said first residue vapors with at least part of a liquid portion of the partially condensed second residue in at least one contacting stage and thereafter separating the vapors and liquids from said contacting stage;

(3) supplying the liquids from said contacting stage to the distillation column as a liquid feed thereto; and (4) directing the vapors from said contacting stage into heat exchange relation with said second residue from the distillation column, thereby to supply the cooling of step (1), and thereafter discharging said vapors from the contacting stage;

the improvement further comprising:

(5) recovering a recycle gas stream from an expander-compressor or residue gas compressor;

(6) cooling and partially condensing the recycle stream in said one or more heat exchangers;

(7) expanding the recycle stream thereby further condensing a portion of and cooling the recycle stream;

(8) feeding the expanded recycle stream to a subcooler, whereby the expanded recycle stream is heat exchanged in the subcooler with gases from top of a light-ends fractionation column thereby providing colder temperatures to the second residue from the distillation column.

14. The process as claimed in claim 13 wherein said contacting step (2) is carried out in the light end fractionation column which includes fractionation means for vapor/liquid counter-current contact and (i) wherein said partly condensed second residue is introduced into said light ends fractionation column above said fractionation means, whereby the liquid portion of the partly condensed second residue passes downwardly through said fractionation means; and (ii) said at least part of one of said first residue vapors is supplied to said light ends fractionation column below said fractionation means, whereby the first residue vapor rises through said fractionation means in counter-current contact with the liquid portion of the partly condensed second residue.

15. The process as claimed in claim 13 wherein the fractionation means in said light ends fractionation column provide the equivalent of at least one theoretical distillation stage arranged to contact at least part of one of said first residue vapors with the liquid portion of the partly condensed second residue.

16. The process according to claim 13 wherein at least part of one of said first residue vapors are co-mingled with the liquid portion of the partially condensed second residue.

17. The process as claimed in claim 13 wherein at least part of one of said first residue vapors are comingled with both the liquid portion and vapor portion of said partially condensed second residue.

18. The process as claimed in claim 13 wherein the colder temperatures provided by the expanded recycle stream improve the yield of ethane and heavier components from the light-ends fractionation column.

19. The process as claimed in claim 13 wherein said recycle gas stream recovered is further fed through an expander/compressor discharge cooler or residue gas compressor discharge cooler prior to said recycle gas stream being condensed in said one or more heat exchangers.

20. The process as claimed in claim 13 wherein said one or more heat exchangers receives additional gas and liquid flows to cool and partially condense the recycle stream.

21. The process as claimed in claim 20 wherein said additional gas and liquid flows are selected from the group consisting of inlet gas stream, liquid product stream, reboiler fluid stream, side heater fluid stream, refrigerant stream(s) and residue gas stream.

22. The process as claimed in claim 13 wherein said one or more heat exchangers is a plate-fin exchanger, shell and tube heat exchanger or coil wound heat exchanger.

23. The process as claimed in claim 13 wherein said expanding of the recycle stream is through a flow control valve or turboexpander.

24. The process as claimed in claim 13 wherein a cold reflux stream is from the distillation column.

* * * * *